(12) United States Patent
Olejnik et al.

(10) Patent No.: US 7,390,318 B2
(45) Date of Patent: Jun. 24, 2008

(54) NEEDLELESS MICROPROTRUSION ELASTOPLAST SYSTEM

(75) Inventors: Orest Olejnik, Coto De Caza, CA (US); Robert T. Lyons, Laguna Hills, CA (US); Scott J. Gerondale, Mission Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/600,576

(22) Filed: Nov. 16, 2006

(65) Prior Publication Data

US 2007/0098773 A1 May 3, 2007

Related U.S. Application Data

(62) Division of application No. 10/915,792, filed on Aug. 10, 2004, now abandoned.

(51) Int. Cl.
*A61M 5/00* (2006.01)

(52) U.S. Cl. .......................... 604/173; 604/142; 604/27; 604/290; 604/890.1

(58) Field of Classification Search ................. 604/142, 604/506, 173; 606/167, 215
See application file for complete search history.

(56) References Cited

U.S. PATENT DOCUMENTS 6,565,532 B1 * 5/2003 Yuzhakov et al. ........... 604/142

* cited by examiner

*Primary Examiner*—Kevin C. Simmons
*Assistant Examiner*—Phillip Gray
(74) *Attorney, Agent, or Firm*—Martin Voet; Brent A. Johnson

(57) ABSTRACT

A needleless microprotrusion system for infusion of a medicament into a patient includes a plurality of microprotrusions having a length sufficient to penetrate a stratum corneum of the patient. A chemodenervating agent is disposed for delivery by the microprotrusions and a substrate is provided for supporting the microprotrusions and conforming the microprotrusions to a patient's palm in order to enable uniform penetration of the microprotrusions into the corneum.

9 Claims, 4 Drawing Sheets

NEEDLELESS MICROPROTRUSION ELASTOPLAST SYSTEM

The present application is a division of U.S. patent application Ser. No. 10/915,792 filed Aug. 10, 2004 now abandoned and this referenced application is to be incorporated in toto herewith by this specific reference thereto.

The present invention is generally directed to a delivery system for a medicament and is more particularly directed to a needleless microprotrusion system for infusion of a medicament into a patient.

Still more particularly, the present invention relates to a novel method of administering chemodenervating agents in a controlled and reproducible manner so as to confine effectiveness of the agent to a given region while minimizing the effects of the agent on adjacent tissue.

Chemodenervating agents such as, for example, botulinum toxin, has been found effective for the treatment of hyperhidrosis and other dermological indications, such as glabellar lines and brow furrow. Current therapies include topicals, that is, for example, antiperspirants, creams and systemic products. All to often these are short acting and/or ineffective.

As noted, a significant advantage in ameliorating sweating and removing wrinkle lines has been achieved through the action of botulinum toxin injections. While this specific treatment is revolutionary and efficacious, the patient is unfortunately placed under significant amount of duress and discomfort due to need to administer multiple injections.

In addition, since each injection represents a possibility for infection, the injections are typically spaced apart from one another, which results in peak and valley concentrations of the medicament.

The epithelia layer of the skin, also referred to as the epidermis, is a part of the skin which provides a barrier against penetration and consists of four layers. These layers are an outermost layer called the stratum corneum and three underlying layers called the stratum granulosum, the stratum malpighii, and the stratum germinativum.

The present invention provides for a system for intradermal administration of neurotoxins in the treatment of hyperhidrosis, skin wrinkles including facial lines.

SUMMARY OF THE INVENTION

The present invention provides for a needleless microprotrusion system for infusion of a medicament into a patient which includes a plurality of microprotrusions having a length sufficient to penetrate a stratum corneum of the patient and a chemodenervating agent disposed on or in the microprotrusions.

A substrate is provided for supporting the microprotrusions with the substrate. The substrate features a shape for conforming to a selected patient body part in order to enable uniform penetration of the microprotrusions into the stratum corneum.

In one embodiment of the present invention, two pluralities of microprotrusions are provided with one plurality of microprotrusions disposed on one side of the substrate and another plurality of microprotrusions disposed on another side of the substrate.

A preferred shape for this embodiment includes a substrate sized for positioning within the palm of a patient and preferably the chemodenervating agent in accordance with the present invention comprises botulinum toxin, preferably type A.

A method in accordance with the present invention utilizing this embodiment basically includes the steps providing a substrate having a shape for conforming to the palm of a patient with the substrate having microintrusions disposed on opposite sides of the substrates. The substrates have a length sufficient to penetrate the stratum corneum of the patients' palm.

A chemodenervating agent is provided for delivery by the microprotrusions and the patent is instructed to dispose the substrate on one palm and press the other palm against the substrate in order to effect simultaneous delivery of the chemodenervating agent into both palms.

In another embodiment of the present invention a substrate is size and shaped for conforming to a patients armpit and in yet another embodiment of the present invention the substrate is sized and shaped for application to a glabellar region of the patient.

In addition, an adhesive disposed on the substrate may be provided for temporarily adhering the substrate to a patients' skin at a selected location and is suitable for receiving the size and shape of the substrate.

To further enhance uniform penetration of the microprotrusions into the stratum corneum, the substrate is preferably flexible.

BRIEF DESCRIPTION OF THE DRAWINGS

The present invention may be more clearly understood with reference to the following detailed description in conjunction with the appended drawings, of which:

FIG. 1 is a side view of one embodiment of the present invention generally showing two pluralities of microprotrusions disposed on opposite sides of a substrate;

FIGS. 2 and 3 illustrate the use of the system shown in FIG. 1 which includes a substrate sized for positioning within the palm of a user;

FIGS. 4-5 show other embodiments of the system in accordance with the present invention utilizing a single plurality of microprotrusions and a substrate for supporting the microprotrusions and having a shape for conforming to a selected body part along with an adhesive for temporarily adhering a substrate to a patients' skin;

FIGS. 6 and 7 illustrate application of the embodiment shown in FIG. 4 and 5;

FIG. 8 shows an alternative embodiment of the present invention in which the substrate is sized and shaped for fitting the fossa axillaris (armpit) of a patient;

FIG. 9 shows and alternative embodiment of the present invention in which the substrate is sized and shaped for positioning against a users' palm and fingers;

FIG. 10 shows an alternative embodiment of the present invention in whish the substrate is sized and shaped for positioning against a users' sole and toes; and FIG. 11 is an enlarge view of the microprotrusions shown in FIGS. 1 and 4.

DETAILED DESCRIPTION

With reference to FIG. 1, there is shown a needleless microprotrusion system 10 in accordance with the present invention for infusion of a medicament (not shown) into a patient, also not shown in FIG. 1.

The system 10 generally includes two pluralities 12, 14 of microprotrusions 16, 18 disposed on opposite sides 20, 22 of a substrate 24.

The microprotrusions 16, 18 may be of any suitable size and configuration and formed from a metal, preferably stainless steel, or other inert material that are directly embedded into the substrate 22 which is preferably an inert platform such as silicone, or polypropylene. With the proper selection of materials, the microprotrusions and substrate may be formed unitarily.

A chemodenervating agent, preferably botulinum toxin, is disposed on the microprotrusions 16, 18 and covered with a removable liner 32 in a conventional manner, said liner being removable for exposing the microprotrusions 16, 18 for use.

Figure 1:
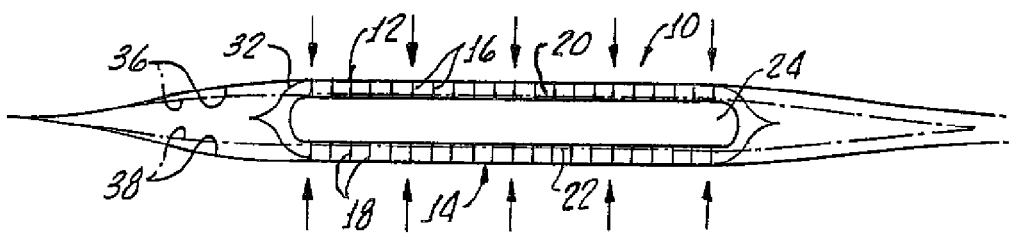
Figure 2:
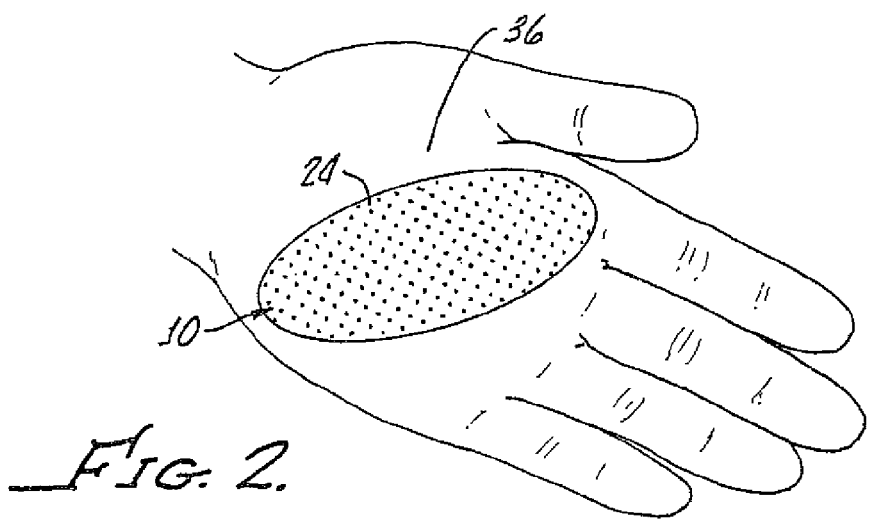
Figure 3:
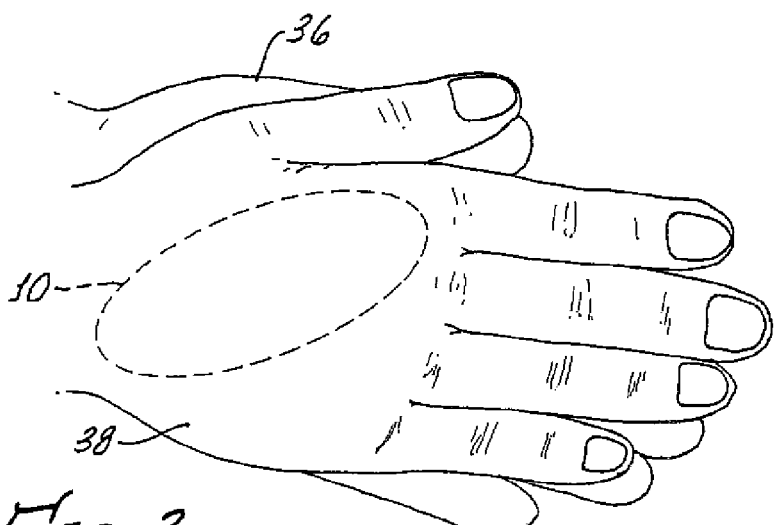

As more clearly shown in FIGS. 2 and 3, the substrate 22 is sized and shaped for conforming to a patients' palm 36 which enables a method in accordance with the present invention as illustrated in FIG. 3 in which a patient, following instructions, disposes the system 10 in one palm 36 and press another palm 38 against the system 10 in order to effect simultaneous delivery of the chemodenervating agent into both palms 36, 38.

This method for delivering the medicament is suitable for treatment of hyperhidrosis. Preferably, the substrate is flexible for enabling uniform penetration of the microprotrusions 16, 18 into the patients' palms 36, 38 respectively. Microprotrusions suitable for use in the present invention are described in U.S. Pat. No. 6,322,808 which is to be incorporated herewith in its entirety for a description of suitable microprotrusions 16, 18 and substrates 24.

Figure 4:
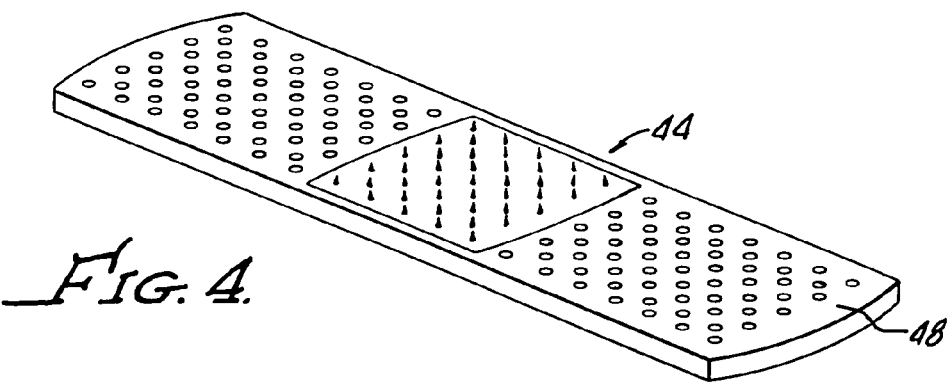
Figure 5:
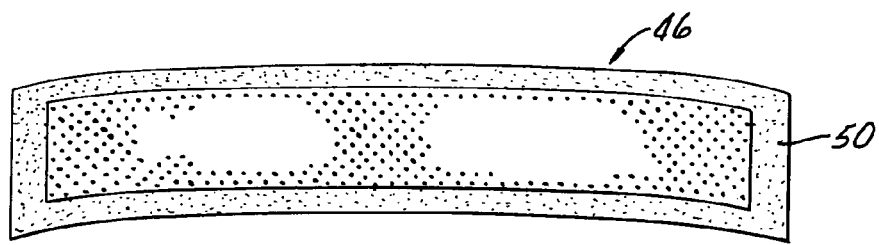
Figure 6:
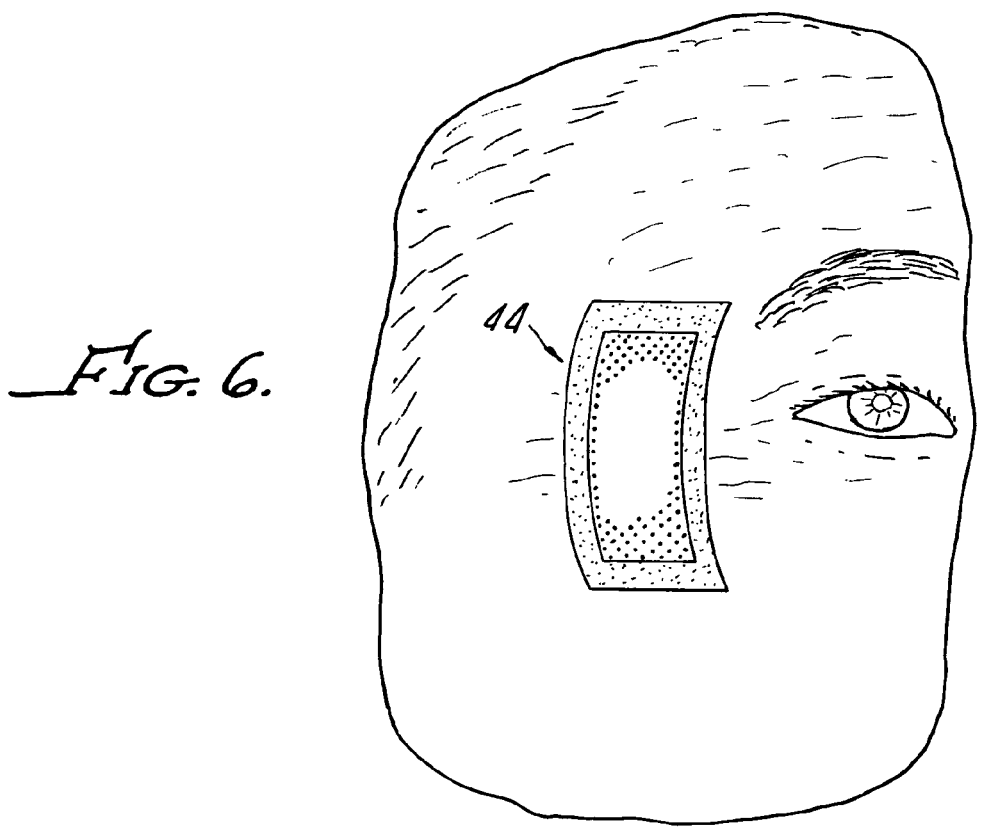
Figure 7:
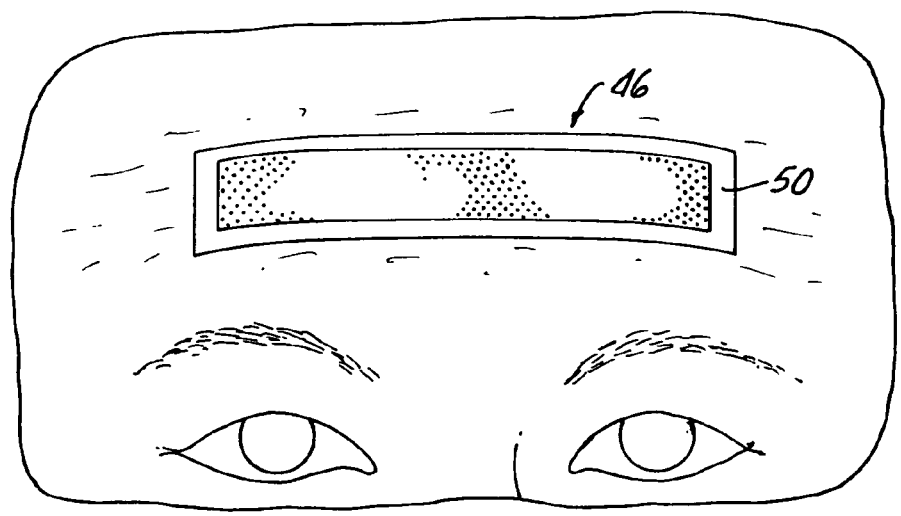

With reference to FIGS. 4 and 5, there are shown alternative embodiments 44, 46 in accordance with the present invention which further include exposed portions 48, 50 respectively which include an adhesive for temporarily adhering the substrate portions 48, 50 to a patient, see FIGS. 6 and 7 respectively which illustrate application of the embodiment 44 for removing wrinkles adjacent a patients' eye and in a glabellar region of the patient.

Figure 8:
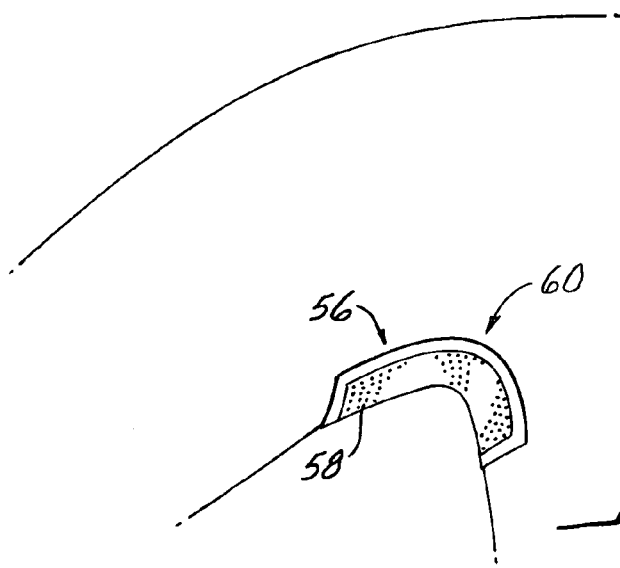

In another embodiment 56 of the present invention as illustrated in FIG. 8 in which a substrate 58 is sized and shaped for fitting and conforming to a patients armpit 60.

Figure 9:
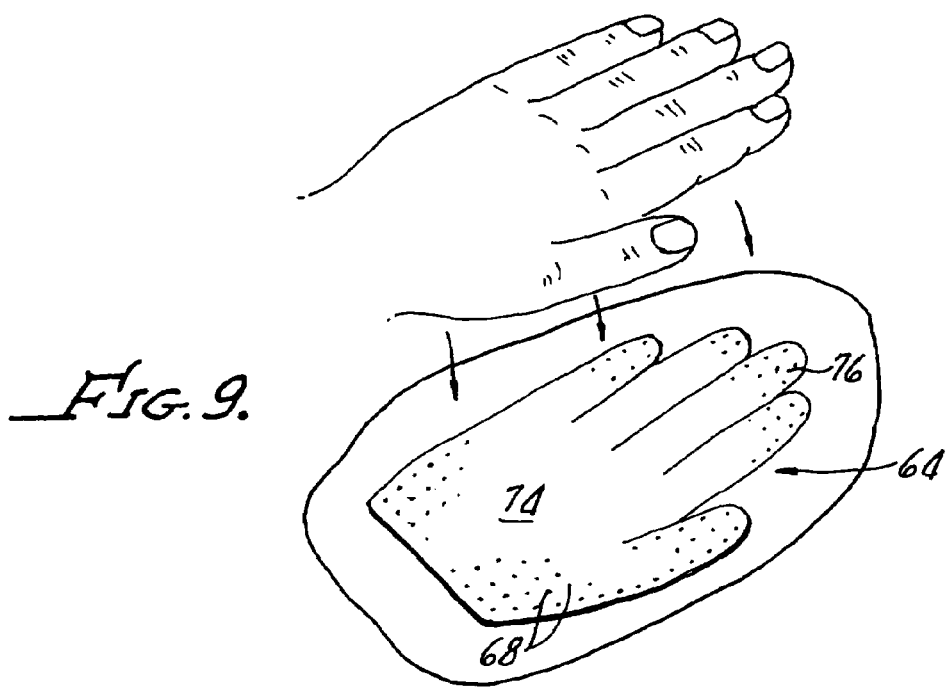
Figure 10:
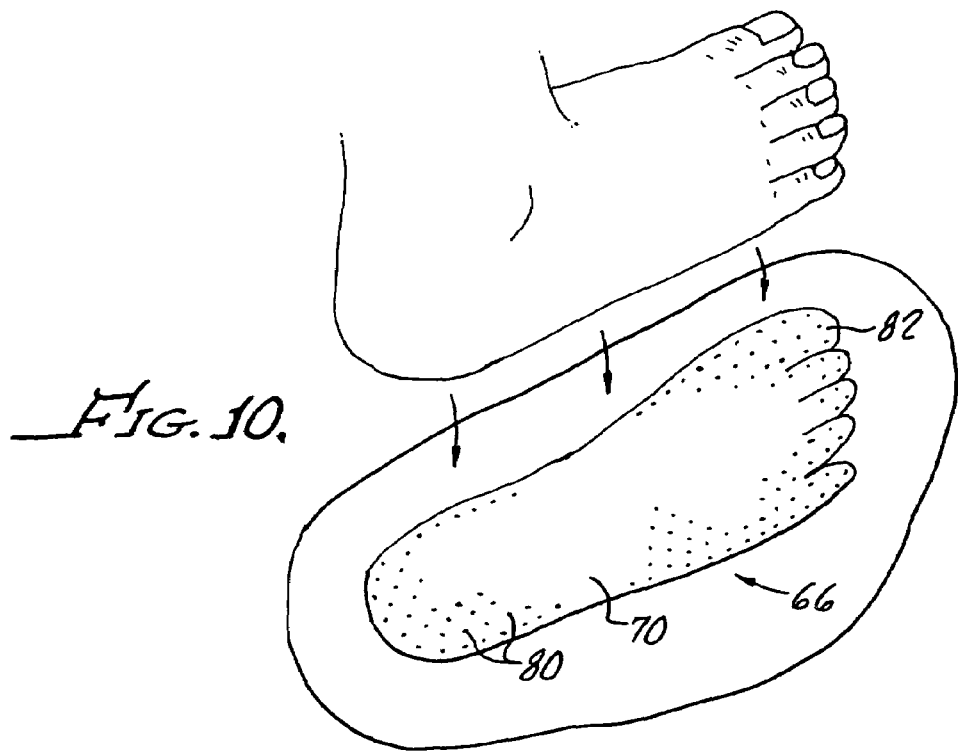

FIGS. 9-10 are alternative embodiments 64, 66 illustrating substrates 68, 70 respectively, which are sized and shaped for positioning against a palm 74 and fingers 76 of a user and for positioning against a sole 80 and toes 80 of a user. Various glove sizes and shoe sizes may be used to produce embodiments 64, 66 for use.

Figure 11:
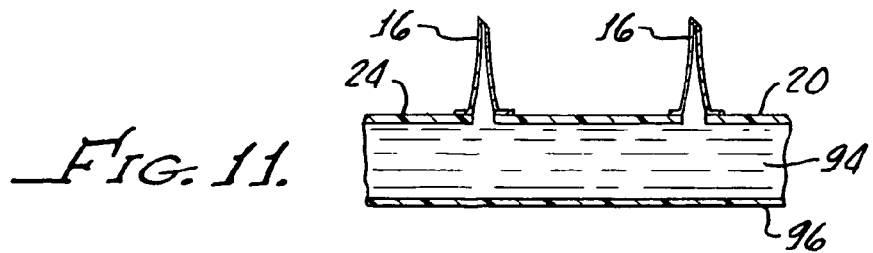

FIG. 11 is an enlarged view of the microprotrusions 16, which as hereinabove noted, may be coated with botulinum toxin or alternatively, filled with a solution including botulinum toxin.

In this instance, a reservoir 90 may be provided behind the microprotrusions 16 and covered by a backing 92 for enabling pressure to be exerted on the reservoir for effecting delivery of the botulinum toxin from the microprotrusion.

It should be appreciated that the length of the microprotrusions are varied depending upon the anatomy of the particular tissue being targeted by the therapeutic neurotoxin.

Although there has been hereinabove described a specific needleless microprotrusion blastoplast system in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A needleless microprotrusion system for infusion of a medicament into a patient, the system comprising:
   a substrate sized and shaped for positioning within a palm of a patient, said substrate having two opposing sides;
   a first plurality of microprotrusions disposed on one opposing side of said substrate;
   a second plurality of microprotrusions disposed on another opposing side of said substrate the first and second pluralities of microprotrusion facing away from each other; and
   a chemodenervating agent disposed for delivery by the first and second pluralities of microprotrusion into the patient's palm.

2. The system according to claim 1 wherein said substrate is flexible.

3. The system according to claim 1 wherein said chemodenervating agent is coated on the first and second pluralities of microprotrusion.

4. The system according to claim 1 wherein said chemodenervating system is disposed within the first and second pluralities of microprotrusions.

5. The system according to claim 1 wherein said chemodenervating agent comprises botulinum toxin.

6. The system according to claim 1 wherein the microprotrusion are hollow and the system further comprises a reservoir disposed between the substrate sides with said chemodenervating agent disposed within said reservoir.

7. A needleless microprotrusion system for infusion of a medicament into a patient, the system comprising:
   a substrate sized and shaped for positioning within a palm of a patient said substrate having two opposing sides;
   a first plurality of hollow microprotrusions disposed on one opposing side of said substrate;
   a second plurality of hollow microprotrusions disposed on another opposing side of said substrate the first and second pluralities of microprotrusion facing away from each other;
   a reservoir disposed between the one and another sides of said substrate;
   a chemodenervating agent disposed in said reservoir for delivery through the first and second pluralities of hollow microprotrusions.

8. The system according to claim 7 wherein said substrate is flexible.

9. The system according to claim 7 wherein said chemodenervating agent comprises botulinum toxin.

* * * * *